United States Patent [19]

Sheridan

[11] Patent Number: 4,990,143
[45] Date of Patent: Feb. 5, 1991

[54] REINFORCED MEDICO-SURGICAL TUBES

[75] Inventor: David S. Sheridan, Argyle, N.Y.

[73] Assignee: Sheridan Catheter Corporation, Argyle, N.Y.

[21] Appl. No.: 506,196

[22] Filed: Apr. 9, 1990

[51] Int. Cl.⁵ ............................................. A61M 25/00
[52] U.S. Cl. ..................................................... 604/282
[58] Field of Search ............... 604/282, 281, 280, 164, 604/170

[56] References Cited

U.S. PATENT DOCUMENTS

| | | |
|---|---|---|
| 2,268,321 | 12/1941 | Flynn . |
| 2,437,542 | 3/1948 | Krippendorf . |
| 2,851,915 | 9/1958 | Martinez . |
| 3,314,430 | 4/1967 | Alley et al. . |
| 3,485,234 | 12/1969 | Stevens . |
| 3,589,368 | 6/1971 | Jackson et al. . |
| 3,605,750 | 9/1971 | Sheridan et al. . |
| 3,618,613 | 11/1971 | Schulte . |
| 3,625,793 | 12/1971 | Sheridan et al. . |
| 3,684,605 | 8/1972 | Zwart . |
| 3,725,522 | 4/1973 | Sheridan et al. . |
| 3,755,525 | 8/1973 | Sheridan et al. . |
| 3,973,569 | 8/1976 | Sheridan et al. . |
| 4,210,478 | 7/1980 | Shoney . |
| 4,655,771 | 4/1987 | Wallsten ......................... 604/281 X |
| 4,665,604 | 5/0019 | Dubowik ......................... 604/282 X |
| 4,690,175 | 9/1987 | Ouchi et al. ......................... 604/282 |
| 4,737,153 | 4/1988 | Shimamura et al. ................. 604/282 |
| 4,863,442 | 9/1989 | DeMello et al. ..................... 604/282 |

FOREIGN PATENT DOCUMENTS 1199761 1/1986 Canada .
2043201 2/1979 United Kingdom .

Primary Examiner—John D. Yasko
Attorney, Agent, or Firm—Burns, Doane, Swecker & Mathis

[57] ABSTRACT

A reinforced medico-surgical tube comprising a tube of flexible material, a filament helix coaxial with the tube and disposed between inner and outer peripheries of the tube, and a distal end of the tube, the distal end including a straight-cut or angle-cut axial end face disposed at an angle equal to or other than 90° with respect to a central axis of the tube. The filament helix is separated into pieces at the distal end if the tube is angle-cut such that coils of the filament helix are discontinuous with opposite ends of the the coils adjacent the end face of the distal end. The cut filament end in the case of a straight-cut tube or the cut filament ends in the case of an angle-cut tube confront the axial end face and are separated therefrom by a thin layer of flexible material formed by melting the end face, melting a plastic piece onto the end face or by any other suitable method. The end face can be radiused to provide a smooth rounded surface extending between the inner and outer peripheries of the tube at the distal end thereof. One or more eyes can extend between the inner and outer peripheries of the tube at the distal end thereof and one or more secondary lumens can be provided in the tube.

14 Claims, 2 Drawing Sheets

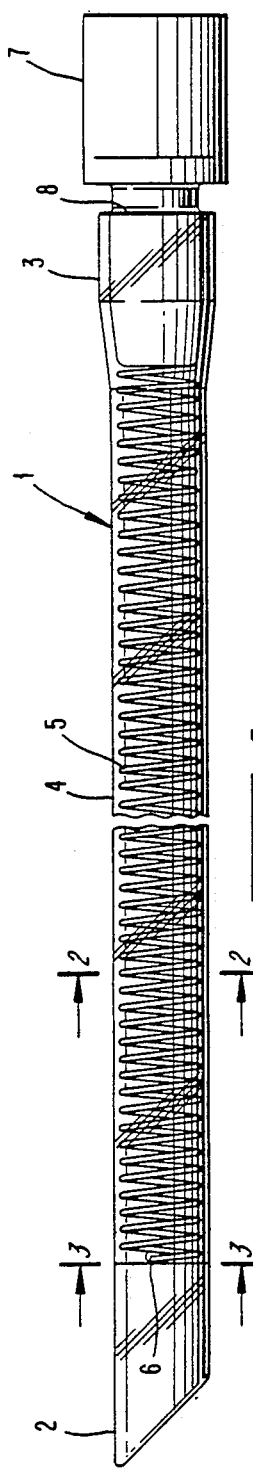
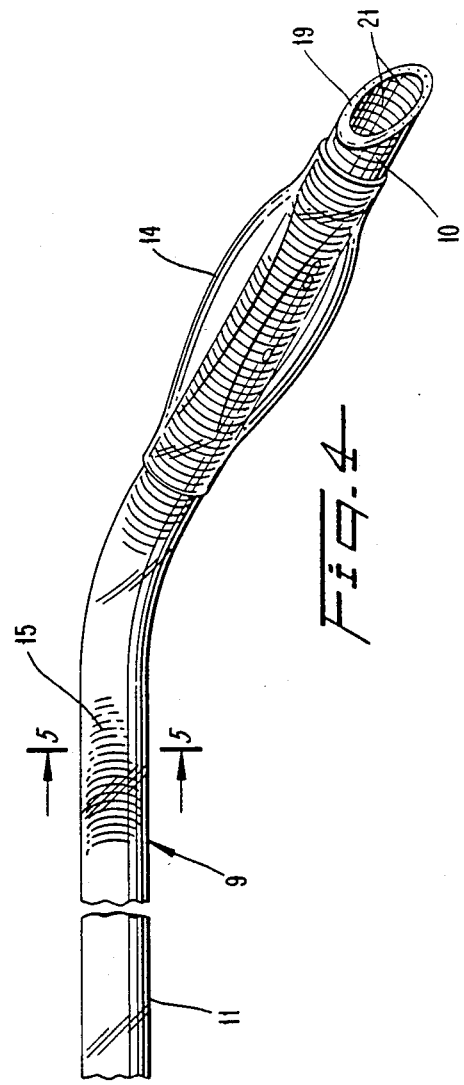
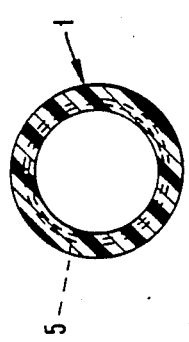
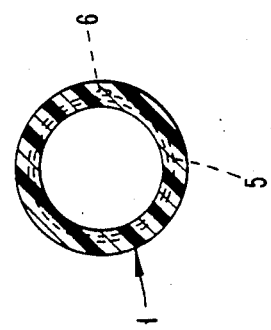
Fig. 1 (PRIOR ART)
Fig. 2 (PRIOR ART)
Fig. 3 (PRIOR ART)
Fig. 4

REINFORCED MEDICO-SURGICAL TUBES

BACKGROUND OF THE INVENTION

1. Field of the Invention

This invention relates to the manufacture of reinforced catheters, tracheal tubes, tracheotomy tubes and other medico-surgical tubes and to the resulting products. More particularly, it concerns the production of medico-surgical tubes that have a central body portion containing a helix of a rigid plastic filament that serves to strengthen the tubes so as to resist kinking and collapsing during use.

2. Description of the Prior Art

This invention relates to uncuffed and balloon-type catheters, i.e., catheters which may be provided at the distal end with an inflatable balloon or cuff which serves, during the medical or surgical procedure performed using the catheter, to retain the catheter in a desired position within the patient, to seal a passage in the patient, etc.

Medico-surgical tubes may assume a variety of sizes, shapes and be provided with a variety of fluid openings, couplings, connectors or the like. Terminology applied to such devices by users, e.g., physicians, surgeons, hospitals, etc., frequently refer to them as catheters, e.g., rectal catheters, urethral catheters, hemostatic catheters and the like, but in other cases they are referred to as tubes, e.g., endotracheal tubes, feeding tubes, suction tubes, drain tubes and the like. For the sake of brevity in describing the improved devices of the invention and their method of production, the term "catheter" is employed throughout the specification and accompanying claims to encompass pertinent medicosurgical devices whether they be popularly referred to by the medical profession and other users as "catheters" or "tubes."

Many forms of medico-surgical tubes that comprise a lumen through which fluids may be passed to or from the body of a patient are known. The simplest of these are the catheters (see U.S. Pat. Nos. 2,437,542; 2,857,915; 3,485,234; 3,605,750; 3,618,613; and 4,210,478). More complex medico-surgical tubes include endotracheal tubes (see U.S. Pat. Nos. 3,625 793; 3,684,605; 3,725,522 and 3,755,525), post surgical tubes (see U.S. Pat. No. 3,589,368), tracheotomy tubes (see U.S. Pat. No. 3,973,569), sump drain tubes (see U.S. Pat. No. 3,314,430) tubes for urological use (see U.S. Pat. No. 2,268,321) and esophogeal endoprosthesis tubes. The present invention provides an improved medico-surgical tube and a method for the production thereof, the medico-surgical tube having a novel distal end.

It is desirable with most types of medico-surgical tubes that they be flexible and have as thin a wall as possible. There is a trade-off, however, in constructing the medico-surgical tube with thin walls and high flexibility, i.e., the thinner and more flexible the tube, the greater the possibility the tube will kink or collapse during use. Since kinking or collapsing can result in complete closure of the lumen with attendant damage or death to the patient, medico-surgical tubes must be structured so as to mitigate kinking.

One way the industry has developed to provide medico-surgical tubes with increased strength but not necessarily with low kinking potential is to include in them a braided wire sheathing embedded between plastic layers (see Great Britain Patent Publication No. GB 2043201A) or a helix of metal wire or synthetic filament (see Canadian Patent No. 1,199,761). Such helix containing tubes are referred to in the trade as "reinforced." In the reinforced tubes, the spacings between coils of the helix are quite small, e.g., 1–3 mm, and are to be contrasted to catheters and like tubes comprising filaments to increase tensile or burst strength, rather than compressive strength (see U.S. Pat. No. 2,268,321). The distal end of the catheter shown in FIGS. 11–13 of U.S. Pat. No. 2,268,321 is not reinforced by a filament helix such that a plurality of coils of the filament helix is provided in the distal end.

Metal wire reinforced tubes, however, are disadvantageous in that they will not spring back when partially collapsed. For instance, if a patient bites down on a metal wire reinforced tracheal tube, the metal wire would be deformed beyond its elastic limit such that the tube remains in a collapsed condition. Such collapsing of the tube can result in nearly complete closure of the lumen with attendant hazard to the patient. Filament reinforced tubes, on the other hand, are more resistant to kinking and crushing because they can spring back when collapsed.

Various methods are known in the art for producing a distal end on such medico-surgical tubes. For instance, a continuous, extruded tube can be square-cut at the proximal end and have a bevel or angle-cut at the distal end. In pure plastic without reinforcing this cutting is straight forward. Subsequent finishing of the distal end can be accomplished by pushing the angle cut end into a heated mold that melts the PVC and forms it into the shape of the mold (see U.S. Pat. No. 3,725,522 and Canadian Patent No. 1,199,761). With this technique, the square edges of the angle cut tip can be made smooth and radiused. An eye can be punched through the long part of the distal end. This can be accomplished by placing a flat mandrel inside the tube and driving a cookie-cutter type punch through the wall.

For extruded tracheal tubes reinforced with wire, however, complicated, and therefore costly end finishing methods have heretofore been used. (See GB 2043201A and Canadian Patent No. 1,199,761). For instance, distal end finishing methods for reinforced tubes include placing a square-cut end into an injection mold, forming the complete tip purely of plastic and at the same time fusing it to the reinforced tube. Alternatively, a pure plastic (wire-free) tip can be made by separately extruding pure plastic tubing of identical ID and OD to the reinforced tube and the tip can be secured to the tube section with solvent or glue. Another method involves stripping of the wire out from between the tube inner and outer walls of a simple square-cut distal tip and the two walls can be welded together with glue after which the tip is then angle-cut, heat-mold finished, and eye punched. It may also be possible to provide spaced, helix or sheathing free portions (such as by intermittently stopping the coiling of filament or sheathing about a base tube) and the tube can be cut to form distal ends of the tube in the helix-free portions of the tube.

A prior art catheter 1 shown in FIG. 1 comprises a molded, helix-free distal end 2, a molded, helix-free proximal end 3 and central body portion 4 containing a helix 5 (see FIG. 2). In order to safeguard against the possibility of the distal end of the helix 5 (particularly where it is made of metal wire) penetrating the outer layer of the catheter 1 during its use, a small loop 6 (see FIG. 3) is formed in the distal end of helix 5 prior to forming the molded distal end 2 on the catheter 1. A rigid molded connector 7 has its distal end 8 encircled by a slightly expanded proximal end 3 of the catheter 1.

Prior to the present invention, the production of distal ends of reinforced medico-surgical tubes has been a labor intensive operation (see Canadian Patent No. 1199761 and GB 2043201A). Furthermore, such distal ends have heretofore been provided without reinforcement for increasing compressive strength of the distal ends. The present invention concerns improved methods for production of distal ends of rigid plastic filament reinforced medico-surgical tubes at lower costs and higher degree of uniformity of product than has been possible heretofore.

SUMMARY OF THE INVENTION

A principal object of the present invention is the provision of a novel reinforced medico-surgical tube and a new method for the production of the distal end of such a reinforced medico-surgical tube.

An object of the present invention is to provide a catheter that is filament reinforced all the way to the distal end (i.e. tip) thereof and finished in a manner smooth enough for intubation. It is expected that the invention will be of very great commercial value as it may replace all metal wire reinforced medical tubes, at least metal wire reinforced tracheal tubes. The non-metallic filament reinforced tube with smooth tip finish according to the invention will be superior in many cases and will be much more economical to produce than a metal wire reinforced tube.

In a preferred embodiment, a medico-surgical tube is reinforced with a filament helix such that a plurality of coils of the filament helix is provided at a distal end of the tube, the tube is simply angle cut or square cut to form the distal end without stripping or other operations, and then the distal end is finished with relatively simple methods. In particular, the medico-surgical tube can comprise a filament reinforced tracheostomy or tracheal tube with the filament extending all the way to the end face at the distal end and the distal end is finished in a simple manner.

According to the present invention, reinforced medico-surgical tubes can be made by a new method which comprises first extruding a continuous, flexible base tube, cooling the extruded tube, coiling a helix of filament about the cooled tube, then extruding an outer layer onto the helix and base tube to form a laminated final tube, cutting the final tube into sections of predetermined length and finally forming at least one filament containing distal end on each cut section of the final tube.

The filament containing distal end may be finished by inserting a donut-shaped piece of plastic in a heated mold prior to inserting the end of a cut section of the final tube in the mold and molding the piece of plastic onto the tube section whereby a radiused tip or end face is formed on the end of the tube. Alternatively, the filament containing end may be finished by simply melting the filament containing distal end of a cut section of final tube.

BRIEF DESCRIPTION OF THE DRAWINGS

The invention will now be described with reference to the drawings, in which:

FIG. 1 is a lateral view of a prior art catheter;
FIG. 2 is a sectional view taken on the line 2—2 of FIG. 1;
FIG. 3 is a sectional view taken on the line 3—3 of FIG. 1;
FIG. 4 is a fragmentary isometric view of a medico-surgical tube made in accordance with the invention.

DETAILED DESCRIPTION OF THE PREFERRED EMBODIMENTS

Figure 5:
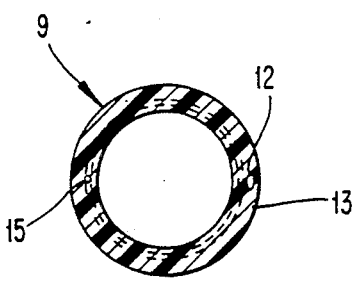
FIG. 5 is a sectional view taken on the line 5—5 of FIG. 4.

The medico-surgical tubes of the invention comprise a medico-surgical tube such as a tracheal tube 9 which includes a filament containing distal end 10 and a proximal end (not shown) joined together by a central body portion 11 (see FIG. 4). The tube 9 has a major lumen that extends the entire length of the tube and can have a secondary lumen 12 formed in a wall 13 of tube 9 (see FIG. 5). The secondary lumen 12 can open near its distal end into a balloon cuff 14 and can be connected at or near its proximal end to an inflation tube (not shown) provided with a pilot balloon (not shown) and a check valve (not shown).

The central body portion 11 of the tube 9 contains a filament helix 15 while the proximal end may be filament-free. The distal end 10, on the other hand, includes means comprising a plurality of coils of the filament helix 15 for providing compressive strength of the distal end 10 as compared to a tube which does not contain such a filament helix. The tube 9 can be made of flexible material, e.g., plasticized polyvinyl chloride, polyurethane, silicone rubber or similar material, while a connector element (not shown) attachable to the proximal end the tube 9 can be molded from rigid material, e.g., nylon, polypropylene, acrylic resin, polystyrene or the like.

Tracheal tubes such as tube 9 are made in a variety of sizes. Typically such tubes will be about 10 to 40 cm in length with the inner diameter ("I.D.") of the major lumen between about 2.0 to 10.0 mm and with the outer diameter ("O.D.") of about 2 to 3 mm greater than the diameter of the major lumen. Other types of tubes in accordance with the teachings of the invention will have dimensions suitable for the intended use of such tubes.

The helix 15 is preferably formed by a rigid plastic filament having a diameter of about 0.1 to 0.5 mm and the spacing between separate coils of the filament 15 typically can be such that the number of winds per tube diameter is generally over 1 and preferably is 5–10 winds per tube diameter. For instance for a 7 mm I.D. tube, the separation between the coils can be about 1 to 3 mm. The filament diameter and spacing between individual coils, however, can be varied to suit the intended use of the tube. Various types of rigid plastic filaments may be used to form the helix, e.g., nylon monofilaments, polyester filaments, poly(ethylene) terephthalate ("PETP", "PET") and the like.

The production of a tracheal tube, such as tube 9, according to the invention can be performed as follows. First, a continuous tube of flexible material, e.g., plasticized polyvinyl chloride, polyurethane, silicone rubber or the like is extruded. This base tube can have a wall thickness of about one-half the thickness desired in the final tube.

The extruded tube is then cooled by passing it through a cooling bath as it emerges from the extrusion die. Next, a filament is coiled about the cooled tube to form a helix that runs longitudinally along the outer surface of the base tube. In accordance with the invention, the helix can be continuous along the entire length of the base tube. As the helix is wound around the base tube, the assembly is fed through a second extruder where an outer layer is extruded over the combined base tube and helix thereby forming a continuous flexible final tube comprising the helix laminated between the base tube and the outer layer, as shown in FIG. 5. During this second extrusion, at least one secondary lumen 12 can be formed in the outer layer using a suitable die. The outer layer may be formed of the same material as the base layer. Alternatively, the outer and inner layers may be formed of different materials.

According to the invention, the tube 9 is reinforced with filament all the way to the tip, the tip is simply cut square with the end face lying in a plane at an angle of 90° to a central axis of the tube 9 or at an angle with the end face lying in a plane at an angle other than 90° to the central axis of the tube 9. For instance, the distal end can be cut at an angle of about 45° as shown in FIG. 4 without stripping or other operations, and then the tip can be end finished with relatively simple methods.

The method according to the present invention can thus include co-extruding filament reinforced tracheal tubing. The end finishing technique according to the invention is economical and simple on such filament reinforced tubes since the ends of such tubes can be cut off using conventional techniques.

Figure 6:
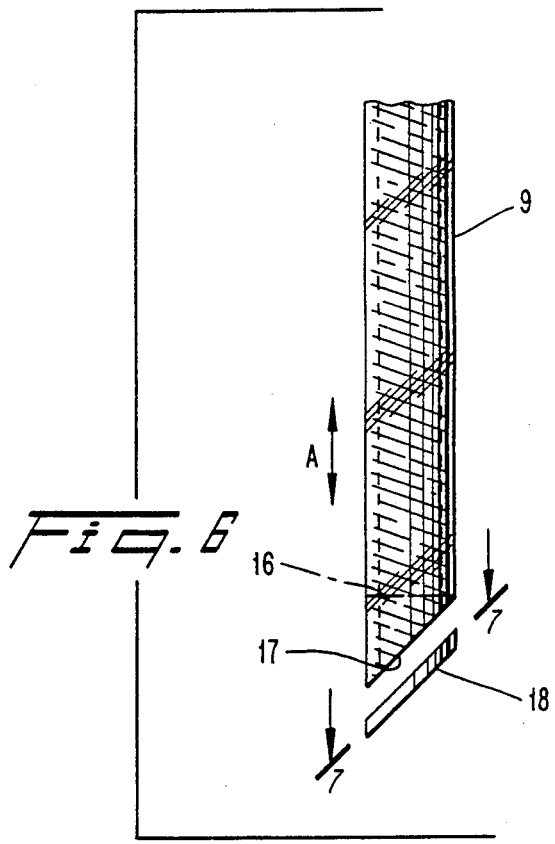
FIG. 6 is a longitudinal cross-section of the tube according to the invention prior to finishing the distal end in a mold using a donut.
Figure 7:
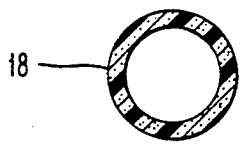
FIG. 7 shows a cross-section of the donut taken along the line 7—7 in FIG. 6.

The end finishing technique according to the invention may involve melting the square-cut 16 or angle-cut 17 end either directly or by placing a small washer-shaped donut 18 (FIGS. 6 and 7) of plastic in a mold (not shown) prior to inserting the distal end 10 of the final tube 9 in the mold. In a preferred embodiment, the piece 18 can have a thickness in the axial direction A (FIG. 6) of about the wall thickness of the final tube and can comprise an annular section of a non-filament containing tube. The axial thickness of the piece 18 should be enough to provide a thin layer which covers the exposed ends of the filament when the piece is melted. Accordingly, after the piece 18 is melted, it covers the raw end or ends 19 of the chopped filament 15 which might otherwise be exposed as cutting edges as the tube 9 is inserted into a body opening such as a trachea. The addition of the plastic piece 18 can be omitted, however, since the ends of the chopped filament can also be suitably covered by a thin layer of material simply by melting the extreme end face of the distal end 10 or by using any other suitable method. The distal end face could be either open or closed.

If the donut of plastic 18 is used, it is also possible to incorporate X-ray opaque pigment therein whereby the opening in the tube can be seen in the body of a patient using X-ray methods.

Figure 8:
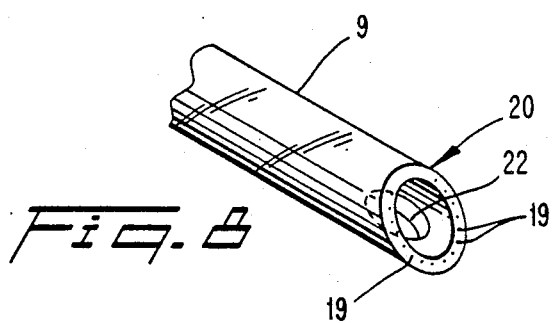
FIG. 8 shows a perspective view of the tube according to the invention prior to the end finishing step.

The reinforced medico-surgical tube of the invention thus comprises a tube 9 of flexible material, a rigid plastic filament helix 15 coaxial with the tube and disposed between inner and outer peripheries of the tube with a plurality of coils of the helix being provided at a distal end 10 of the tube to increase the compressive strength of the distal end, the distal end including an axial end face 20. In the case of the angle-cut end 17, the individual coils of the filament helix 15 are separated into a plurality of discrete pieces at the distal end 10 due to the cutting step. In particular, coils 21 of the filament helix are discontinuous with each other and the free ends 19 of the cut filament are exposed at the end face 20 after the cutting step (see FIG. 8). With the angle cut-end 17, the respective discontinuous coils of the filament become shorter in circumferential length at positions located closer to the axial end face 20, at least some of the discontinuous coils having free opposing ends 19 thereof confronting the axial end face 20 but being spaced inwardly therefrom by a thin layer of flexible material formed by melting the end face 20, by melting the plastic piece 18 onto the end face or by any other suitable method. The thin layer can have a maximum thickness between the end face 20 and a portion of the filament located closest thereto of about twice the distance between adjacent coils of the filament helix 15. For example, the thin layer can have a maximum thickness of about four times the wall thickness of the tube. In addition, an opening or eye 22 can extend between the inner and outer peripheries of the tube at the distal end 10 thereof.

In accordance with the present invention it is possible to produce reinforced medico-surgical tubes at much less cost and with greater uniformity than has been possible heretofore so that they may be treated as one-use, disposable items. The resulting products can be individually packaged and then sterilized, e.g., by exposure to ethylene oxide gas or to cobalt 60 radiation, so that the physician or other user can use the product immediately upon removal from the sterile package.

The invention is proposed for use in manufacture of all types of reinforced medico-surgical tubes now used or later developed for use by the medical profession.

While the invention has been described with reference to the foregoing embodiments, changes and variations may be made thereto which fall within the scope of the appended claims.

What is claimed is:

1. A reinforced medico-surgical tube comprising:
   a tube of flexible material;
   a filament helix coaxial with the tube and disposed between inner and outer peripheries of the tube and extending along the tube to a distal end thereof; and
   means comprising a plurality of coils of the filament helix at the distal end for providing increased compressive strength of the distal end, the distal end including a distal end face, the filament helix being separated from the distal end face by a thin layer of flexible material such that a cut filament end of the helix is not exposed at the distal end face.

2. The tube of claim 1, wherein the end face lies in a plane at an angle of other than 90° to a central axis of the tube, the filament helix including a plurality of cut filament ends confronting said plane, at least some of the coils of the filament helix being discontinuous with each other and the circumferential length of the coils being shorter at positions located closer to the axial end face, at least some of the coils having opposite ends thereof confronting the axial end face and separated therefrom by said thin layer of material.

3. The tube of claim 1, further comprising at least one eye extending between the inner and outer peripheries of the tube at the distal end thereof.

4. The tube of claim 2, wherein said thin layer of material separating the opposite ends of the coils from the axial end face comprises a melted washer-shaped piece of material.

5. The tube of claim 4, further comprising at least one secondary lumen disposed between the inner and outer peripheries of the tube.

6. The tube of claim 5, wherein the at least one secondary lumen is disposed between the filament helix and the outer periphery of the tube.

7. The tube of claim 1, wherein the coils of the filament helix are separated from each other in a direction parallel to a central axis of the tube such that the number of the winds of the helix per tube diameter is over 1.

8. The tube of claim 7, wherein the filament has a diameter of about 0.1 to 0.5 mm.

9. The tube of claim 1, wherein the end face comprises a smooth radiused edge extending between the inner and outer peripheries of the tube.

10. The tube of claim 1, wherein the thin layer has a maximum thickness between the end face and a portion of the filament located closest thereto of about four times the thickness of the wall of the tube.

11. The tube of claim 1, wherein the end face lies in a plane at an angle of 90° to a central axis of the tube.

12. The tube of claim 7, wherein the number of winds per tube diameter is in the range of 5 to 10.

13. The tube of claim 1, wherein the distal end face includes an axially extending opening there through.

14. The tube of claim 1, wherein the distal end face is closed.

* * * * *